(12) United States Patent
Hamilton et al.

(10) Patent No.: US 10,607,454 B2
(45) Date of Patent: Mar. 31, 2020

(54) DEVICE MANAGEMENT PORTAL, SYSTEM AND METHOD

(75) Inventors: Carol J. Hamilton, Fife (GB); Sharon J. Dickie, Dundee (GB)

(73) Assignee: NCR Corporation, Atlanta, GA (US)

( * ) Notice: Subject to any disclaimer, the term of this patent is extended or adjusted under 35 U.S.C. 154(b) by 2464 days.

(21) Appl. No.: 12/004,356

(22) Filed: Dec. 20, 2007

(65) Prior Publication Data

US 2009/0164250 A1 Jun. 25, 2009

(51) Int. Cl.
*G07F 19/00* (2006.01)
*G06Q 10/06* (2012.01)
*G06Q 50/24* (2012.01)
*G06Q 20/18* (2012.01)

(52) U.S. Cl.
CPC ....... *G07F 19/20* (2013.01); *G06Q 10/06393* (2013.01); *G06Q 20/18* (2013.01); *G06Q 50/24* (2013.01); *G07F 19/207* (2013.01); *G07F 19/211* (2013.01)

(58) Field of Classification Search
CPC .......................... G07F 19/20; G06Q 10/06393
USPC .......................................................... 705/52
See application file for complete search history.

(56) References Cited

U.S. PATENT DOCUMENTS

| | | | | |
|---|---|---|---|---|
| 5,515,377 | A * | 5/1996 | Horne et al. | 370/395.64 |
| 6,618,396 | B1 * | 9/2003 | Kondo et al. | 370/474 |
| 6,721,713 | B1 * | 4/2004 | Guheen et al. | 705/1.1 |
| 7,062,294 | B1 * | 6/2006 | Rogard et al. | 455/562.1 |
| 7,069,274 | B2 * | 6/2006 | Stern | 705/26.1 |
| 7,184,423 | B2 * | 2/2007 | Bryan et al. | 370/338 |
| 7,287,010 | B1 * | 10/2007 | Ishibashi | 705/52 |
| 7,383,191 | B1 * | 6/2008 | Herring et al. | 705/1.1 |
| 2002/0199009 | A1 * | 12/2002 | Willner et al. | 709/231 |
| 2003/0055689 | A1 * | 3/2003 | Block et al. | 705/5 |
| 2003/0061271 | A1 * | 3/2003 | Pittarelli | 709/203 |
| 2003/0134648 | A1 * | 7/2003 | Reed et al. | 455/456 |
| 2003/0191623 | A1 * | 10/2003 | Salmonsen | 703/24 |
| 2004/0215566 | A1 * | 10/2004 | Meurer | 705/43 |
| 2004/0266336 | A1 * | 12/2004 | Patsiokas et al. | 455/3.04 |
| 2005/0006468 | A1 * | 1/2005 | Fandel et al. | 235/383 |
| 2005/0132070 | A1 * | 6/2005 | Redlich et al. | 709/228 |
| 2005/0240558 | A1 * | 10/2005 | Gil et al. | 707/1 |
| 2005/0278270 | A1 * | 12/2005 | Carr et al. | 706/25 |
| 2006/0047573 | A1 * | 3/2006 | Mitchell et al. | 705/14 |
| 2006/0059253 | A1 * | 3/2006 | Goodman et al. | 709/223 |
| 2007/0118389 | A1 * | 5/2007 | Shipon | 705/1 |

(Continued)

FOREIGN PATENT DOCUMENTS

EP 0977163 A2 2/2000

*Primary Examiner* — Jay Huang
(74) *Attorney, Agent, or Firm* — Schwegman, Lundberg & Woessner

(57) ABSTRACT

A device management system comprises a processor, a data storage device and a network connection. The data storage device stores weighting data associated with at least one ATM. The processor receives performance metric data from the ATM via the network connection and accesses the weighting data from the data storage device. The processor weights a portion of the performance metric data associated with the ATM with respect to a portion of weighting data associated with the ATM, to produce weighted performance data. The weighted performance data is used in estimating the number of customers unserved during a period of downtime of the ATM.

16 Claims, 5 Drawing Sheets

(56) References Cited

U.S. PATENT DOCUMENTS

2008/0043617 A1* 2/2008 Schekochikhin et al. .... 370/229
2008/0049616 A1* 2/2008 Kamath et al. ............... 370/235
2008/0109796 A1* 5/2008 Kosche ......................... 717/158
2008/0168135 A1* 7/2008 Redlich et al. ............... 709/204
2009/0100459 A1* 4/2009 Riedl et al. ..................... 725/35

* cited by examiner

DEVICE MANAGEMENT PORTAL, SYSTEM AND METHOD

FIELD OF THE INVENTION

The present invention relates to a device management portal, system and method. More particularly, but not exclusively, the invention relates to a device management portal, system and method that manages a distributed network of self-service devices.

BACKGROUND TO THE INVENTION

Typically, in IP networks of managed devices, such as automated teller machines (ATMs), a simple network management protocol (SNMP) agent runs on each device in the network. These SNMP agents collect performance metric data relating to the operation of the managed devices and send alert messages when a device malfunctions.

Typically, the performance metric data collected by an SNMP agent is in a proprietary format. These proprietary data formats require translation by the SNMP agent into an SNMP compatible form for transmission across a communications network to a network management system (NMS). The NMS runs applications that manage and control the managed devices.

In the case of a network of ATMs, each ATM runs an agent, for example an SNMP agent that monitors a number of performance metrics associated with the operation of the ATM including, inter alia, the downtime of each ATM. It will be understood that the term downtime is used herein to refer to time during which the ATM cannot be used for carrying out transactions, either withdrawal or deposit.

Typically, older ATMs, sometimes referred to a "legacy systems", monitor downtime using system network architecture (SNA) in which the ATM itself keeps a log of their usage, status and how many operations have taken place in a specified time period, for example how many receipts have been printed since the thermal paper roll was last changed?

Such monitoring of the down time of the ATMs gives a measure of the reliability of the ATM network. However, a simple ATM downtime measurement, in terms of hours and/or minutes, does not give a true measure of the business impact of the ATM downtime on a financial institution. For example, a customer who finds an ATM that is down may complete a transaction in branch, thereby incurring the additional cost for the financial institution of the human involvement of a member of staff in the transaction.

Alternatively, the customer may complete their transaction at the ATM of a second financial institution. The completion of the transaction at the second financial institution's ATM may incur a cost to the first financial institution if the transaction was completed by a customer of the first financial institution, as it becomes a "not on us" transaction. Alternatively, the completion of the transaction at the second financial institution's ATM may reduce charges levied by the first financial institution if the transaction was completed by a customer of another financial institution, as a "not on us" transaction is lost by the first financial institution.

Downtime occurring during an ATM's high usage period, for example lunchtime the day following Thanksgiving, has a greater impact upon the number of customers who cannot be serviced, than downtime during a low usage period or at a low usage ATM. However, using time based current metrics downtime at high usage ATMs, or during high usage periods, contributes equally to an overall downtime measurement as downtime occurring at low usage periods, for example two a.m. on Thanksgiving morning. This is despite the great disparity in the numbers of customers that this downtime would affect.

Recurring instances of ATM downtime at high usage periods affects customer satisfaction, and can ultimately reduce customer retention.

Using current metrics it is not possible to schedule maintenance routes based upon the ATMs currently down that have the greatest customer impact.

Currently, there is no integrated environment in which key performance indicators (KPIs) can be monitored and tracked. This results in a lack of coherent planning and scheduling based upon KPIs.

SUMMARY OF THE INVENTION

According to a first aspect of the present invention there is provided a device management system comprising a processor, a data storage device and a network connection, the data storage device being arranged to store weighting data associated with at least one managed device, the processor being arranged to receive performance metric data from the at least one managed device via the network connection, the processor being arranged to access the weighting data from the data storage device and being further arranged to weight a portion of the performance metric data associated with the at least one managed device with respect to a portion of weighting data associated with the at least one managed device, to produce weighted performance data.

The at least one managed device may comprise a self-service terminal. The at least one managed device may comprise any of the following: ATM, medical record entry terminal, self-check in/out terminal.

The weighting data may comprise at least one of the following: temporal usage data corresponding to a period over which the performance metric data was acquired, fee data corresponding to a fee associated with a transaction, temporal accessibility data corresponding to time periods when the at least one managed device is operable by a user, location data indicative of geographic factors associated with the at least one managed device.

The temporal usage data may comprise historical usage data. The temporal usage data may comprise projected usage. The temporal usage data may comprise a combination of historical and projected usage data.

The fee data may correspond to a historical average of fees associated with a plurality of transactions executed on the at least one managed device. The fee data may be correlated with the temporal usage data.

The accessibility factor may be correlated with the temporal usage data. The accessibility factor may be arranged to exclude selected portions of the temporal usage data.

The processor may be further arranged to rank a plurality of managed devices with respect to values of the weighted performance data.

The weighted performance data may comprise a measure of the number of users unable to perform a transaction at the managed device during a period of downtime of the at least one managed device.

The weighted performance data may comprise a measure of revenue lost by an operator of the at least one managed device during a period of downtime of the at least one managed device.

The weighted performance data may comprise the number of transactions lost during the period over which the performance metric data was captured.

The processor may be further arranged to output a graphical representation of the weighted performance data to a display device via a graphical user interface (GUI).

According to a second aspect of the present invention there is provided a device management method comprising the steps of:

weighting performance metric data, associated with at least one managed device with respect to a respective portion of weighting data associated with the at least one managed device to produce weighted performance data.

The method may comprise the step of weighting the performance metric data by at least one of the following: temporal usage data corresponding to a period over which the performance metric data was acquired, fee data corresponding to a fee associated with a transaction, temporal accessibility data corresponding to time periods when the at least one managed device is operable by a user, location data indicative of geographic factors associated with the at least one managed device. The temporal usage data may comprise historical usage data. The temporal usage data may comprise projected usage. The temporal usage data may comprise a combination of historical and projected usage data.

The fee data may correspond to a historical average of fees associated with a plurality of transactions executed on the at least one managed device. The fee data may be correlated with the temporal usage data.

The accessibility factor may be correlated with the temporal usage data. The accessibility factor may be arranged to exclude selected portions of the temporal usage data.

The weighted performance data may comprise a measure of the number of users unable to perform a transaction at the at least one managed device during a period of downtime of the at least one managed device.

The weighted performance data may comprise a measure of revenue lost by an operator of the at least one managed device during a period of downtime of the at least one managed device.

The weighted performance data may comprise the number of transactions lost during the period over which the performance metric data was captured.

The method may comprise the step of calculating an estimate of number of users unable to perform a transaction at the managed device during a period of downtime of the at least one managed device, using the weighted performance data.

The method may comprise the step of calculating an estimate of revenue lost by an operator of the at least one managed device during a period of downtime of the at least one managed device, using the weighted performance data.

The method may comprise the step of ranking a plurality of managed devices with respect to values of at least one common weighted performance data set.

The at least one managed device may comprise a self-service device. The self-service device may comprise at least one of the following: an ATM, a medical record entry terminal or a self-check in/out terminal.

The method may further comprise outputting a graphical representation of the weighted performance data to display device via a graphical user interface (GUI).

According to a third aspect of the present invention there is provided a graphical user interface (GUI) portal arranged to display a graphical representation of the weighted performance data of either of the first or second aspects of the present invention to a user.

The GUI portal may comprise a graphical representation of the location of the at least one managed device.

The GUI portal may comprise graphical status indicators indicating the value of each of a plurality of performance metrics associated with the at least one managed device. The graphical status indicators may be arranged to indicate the value of at least one set of weighted performance data.

The GUI portal may comprise a field displaying a ranking of a plurality of managed devices with respect to at least one common weighted performance data set.

The GUI portal may comprise a graphical display of trends in the weighted performance data. The GUI portal may comprise a graphical display of temporal trends in the weighted performance data. The GUI may comprise a graphical display of geographic trends in the weighted performance data.

The GUI portal may comprise at least one selectable user defined graphical display arranged to display a user defined statistic derived from a selection of performance metric data.

According to a fourth aspect of the present invention there is provided software which when executed upon a processor causes the processor to operate as the processor of the first aspect of the present invention.

According to a fifth aspect of the present invention there is provided software which when executed upon a processor causes the processor to execute the method of the second aspect of the present invention.

According to a sixth aspect of the present invention there is provided software which when executed upon a processor causes the processor to generate the GUI portal of the third aspect of the present invention.

According to a seventh aspect of the present invention there is provided a method of scheduling maintenance of a network comprising a plurality of managed devices comprising the steps of:

i) managing the network according to the method of the second aspect of the present invention;

ii) ranking the plurality of managed devices according to a value contained in respective weighted performance data; and iii) determining a priority of maintenance scheduling based upon the ranking of step (ii).

According to eighth aspect of the present invention there is provided a method of reducing downtime of a managed device in a managed network comprising scheduling maintenance of the network according to the sixth aspect of the present invention.

According to an ninth aspect of the present invention there is provided a method of increasing earnings associated with transactions carried out at a managed device comprising reducing the downtime of the managed device according to the seventh aspect of the present invention.

According to a tenth aspect of the present invention there is provided a method of improving brand appeal comprising scheduling maintenance of the network in accordance with the sixth aspect of the present invention further comprising scheduling repairs to the most popular managed devices early in a maintenance cycle.

According to an eleventh aspect of present the invention there is provided a network management tool for managing a group of networked devices, the network management tool comprising a user interface providing a graphical representation of network management data, the network management data including: data representing availability of each device in the network, data representing a number of transactions unfulfilled due to device unavailability, and data representing an amount of valuable media stored in each device in the network.

The network management tool may include a transaction store for receiving from a host anonymized transactions executed by the devices in the network. The network management tool may process the anonymized transactions to create usage models for each device in the network. The network management tool may use the usage models to estimate the number of transactions unfulfilled due to device unavailability.

The network management tool may include, or be coupled to, an automated dispatch system for dispatching a customer engineer to a device in the event of a fault occurring at that device.

The network management tool may provide parameters configurable by an operator of the tool, such parameters may include, a desired range of valuable media in each device, a minimum desired device availability value, and the like.

According to a twelfth aspect of the present invention there is provided a network management tool for managing a group of networked devices, the network management tool comprising: a secure connection to a transaction host; a transaction store for storing transaction data received from the transaction host; a management store for receiving management data from the transaction host; a processor for providing an operator of the network management tool with a unified view of processed transaction information and management information.

The transaction store and management store may be implemented by a common data store, such as a database.

BRIEF DESCRIPTION OF THE DRAWINGS

Embodiments of the present invention will now be described, by way of example only, with reference to the accompanying drawings, in which.

DETAILED DESCRIPTION

Figure 1:
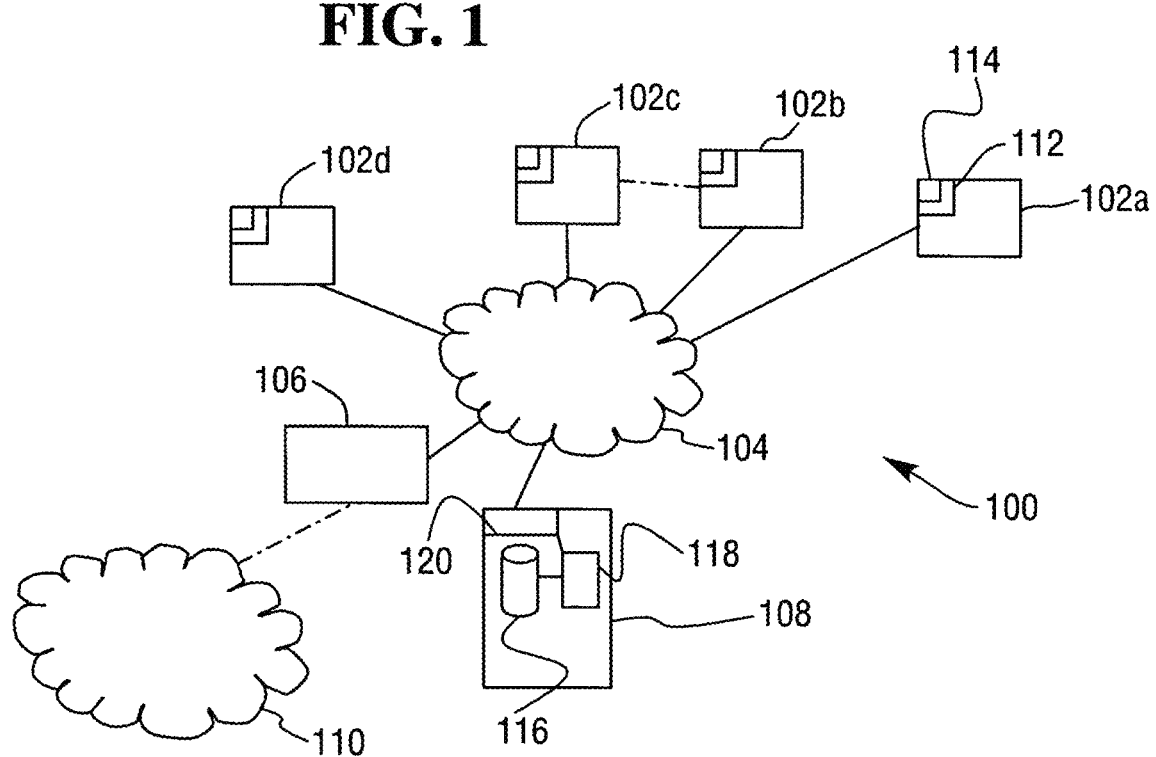
FIG. 1 is a schematic diagram of an embodiment of managed network comprising a device management system according to an aspect of the present invention.

Referring now to FIG. 1, a managed network of ATMs 100 comprises ATMs 102a-d, a communications network 104, an authorization host 106, a management unit 108 and an interchange network 110.

Each ATM 102a-d comprises a processor 112, other features of the ATMs 102a-d will be known to those skilled in the art. Each ATM 102a-d runs a management agent 114 upon their respective processors 112. Typically, the management agent 114 is an SNMP management agent.

The communications network 104 comprises a secure network over which transactions data for transactions executed at the ATMs 102a-d passes to the authorization host 106. Typically, the communications network 104 is a private network or a VPN.

The authorization host 106 authorizes "on us" transactions (that is, where the financial institution operating the ATM network 100 is also the issuer of a card used by the customer), and can route "not on us" transactions to authorization hosts of other financial institutions via the interchange network 110.

The management unit 108 comprises a data storage device 116, a processor 118 and a network connection 120. The data storage device 116 stores temporal usage data for each of the ATMs 102a-d in the managed network 100. Typically, the usage data is historical usage data. For example, the usage data may comprise the average daily usage of each ATM over the previous month. Usually, the daily usage is divided into time periods, such as quarter of an hour or half hourly units.

Alternatively, or additionally, the usage data may be projected usage data. The projected usage data may be calculated from theoretical models based upon population density, spending patterns and the location of an ATM 102a-d. Such projected usage data may be combined with historical usage data to compensate for seasonal trends, or special one off events. For example, in the weeks running up to Christmas an ATM 102a-d located in a shopping mall would be expected to have significantly increased usage over the average for November. Accordingly, a scaling factor to historical data can be used to compensate for this seasonal variation. Similarly, if a major sporting event, such as the Superbowl, or a rock concert is anticipated by a financial institution scaling factors can be applied to historical data to provide improved accuracy of temporal usage data.

The management agent 114 collects status and performance data about the operation of its respective ATM 102a-d. For example, the management agent 114 may receive a status message indicating that and ATM 102a-d is low on banknotes. As another example, the management agent 114 may receive an error message indicating that there is a jam in the receipt printer of an ATM 102a-d. In a third example, the management agent 114 may receive an error message indicating that there is a failure in a critical component, such as a cash dispenser device. The first of the above two examples represent non-critical events that do not necessitate immediate maintenance, whereas the third example constitutes a critical event requiring immediate maintenance.

The management agent 114 then transmits this status and performance data across the communications network 104 to the management unit 108 via the network connection 120. One element of the status and performance data transmitted to the management unit 108 is the time, and duration of downtime, of each ATM 102a-d.

The processor 118 accesses the data storage device 116 and reads the temporal usage data for an ATM 102a-d that has experienced downtime corresponding to the time and duration of the ATM's downtime. The processor 118 weights the downtime with the temporal usage data to provide an estimate of customers who have not been able to fulfill their transaction during the ATM's downtime, an unserved customer (UC) metric.

This UC metric can be used to determine potential lost revenues from ATM downtime. For example, if the ATM suffering the outage is located in a financial institution's own branch the lost revenues may be less than if the ATM is standalone with a competitor's ATM adjacent to it. However, lost revenues will be less if the ATM suffering the outage is one of multiple ATMs operated by the financial institution grouped together as a customer can use another of the grouped ATMs. A flagging of single or grouped ATMs at the NMS improves the accuracy of modeling of lost revenue.

In a further example, an ATM in an airport or tourist attraction may execute a high percentage of credit card transactions, which attract a higher transaction fee than "on us" transactions carried out a neighborhood branch. Thus, the incorporation of a fee compensation factor further improves the accuracy of an estimate of lost revenue associated with ATM downtime. Such a fee compensation factor may be the averaged fee revenue generated by the ATM over a time period, for example one month.

Currently, ATM downtime reflects downtime over twenty four hour period. Whilst this may be appropriate for a 24/7 convenience store or a drive through ATM, it may not be appropriate to an ATM located in a lobby of a financial institution's branch where access is restricted to, for example, nine a.m. to four p.m. Downtime outside of time periods where the ATM is accessible does not impact directly on the business of the financial institution operating the ATM. A usage window that discounts downtime outside of hours where the ATM is accessible can be used to prevent non-impacting downtime being included in UC determination.

Any combination of the above situations can be accounted for in the weighting of the downtime by appropriate user defined weighting factors in order to further improve how accurately the UC KPI models the effect of ATM downtime on a financial institutions business.

It will be appreciated that whilst the above mentioned user defined weighting factors can be applied to the UC KPI the use of user defined weighting factors is optional. Such user defined weighting factors can be defined for a single ATM or a group of ATMs. A grouping of ATMs may be defined by, for example, geographical location, hours of availability, whether the ATM is standalone or grouped, proximity to competitor's ATM or branch.

Once appropriate UC and user defined weightings, if appropriate, have been applied to each ATM 102 *a-d* in the managed network 100 it is possible to rank the ATMs 102*a-d* according to the impact of their downtime on the financial institutions business. Such a ranking allows the scheduling of ATM maintenance on the basis of business impact. This can reduce the downtime of a financial institutions most popular, highest earning or otherwise key ATMs. Such reduced downtime improves customer retention.

Along with ATM downtime a large number of other KPIs are transmitted from the management agent 114 to the management unit 108. Non-limiting examples of such KPIs include ATM availability, cash outs, cash in network, transaction volumes, acceptance or refusal of marketing offers, transaction approval rates, session time per transaction, and incidents causing ATM outage.

Figure 2:
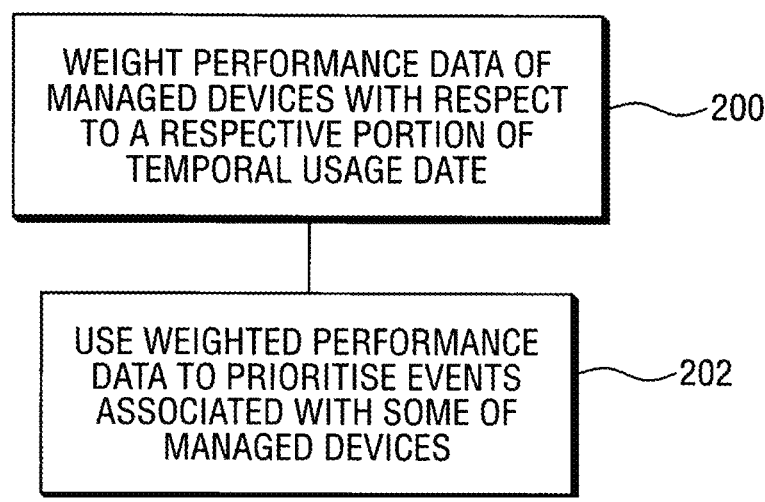
FIG. 2 is flow chart showing the steps of a device management method according to another aspect of the present invention.

Referring now to FIG. 2, a device management method of comprises weighting performance metric data received from a plurality of managed devices with respect to a respective portion of temporal usage data associated with each of the managed devices to produce weighted performance data (Step 200). The weighted performance data is used to prioritize events associated with some of the plurality of managed devices (Step 202).

Figure 3:
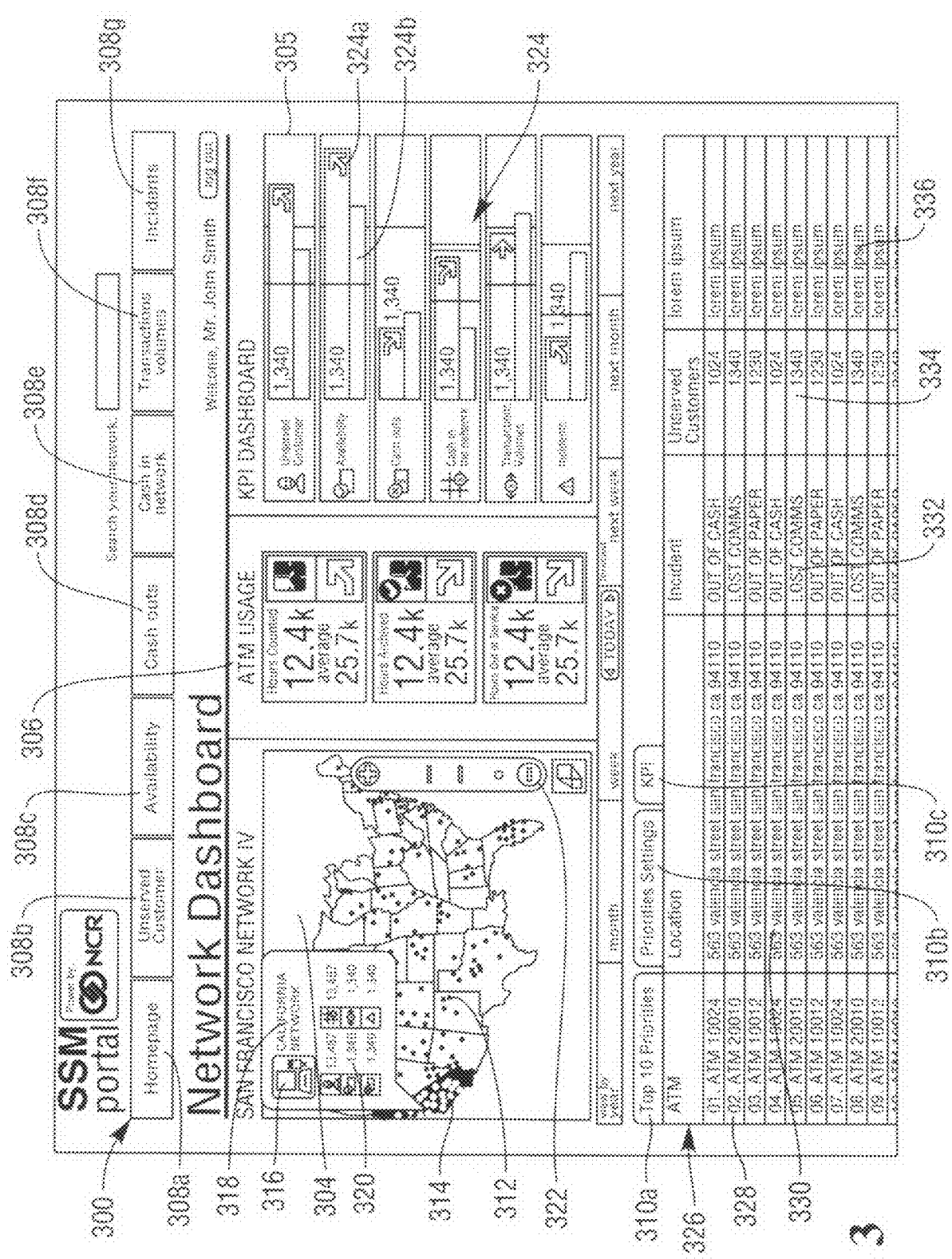
FIG. 3 is a screen shot of a first screen of a GUI portal according to yet another aspect of the present invention.
Figure 4:
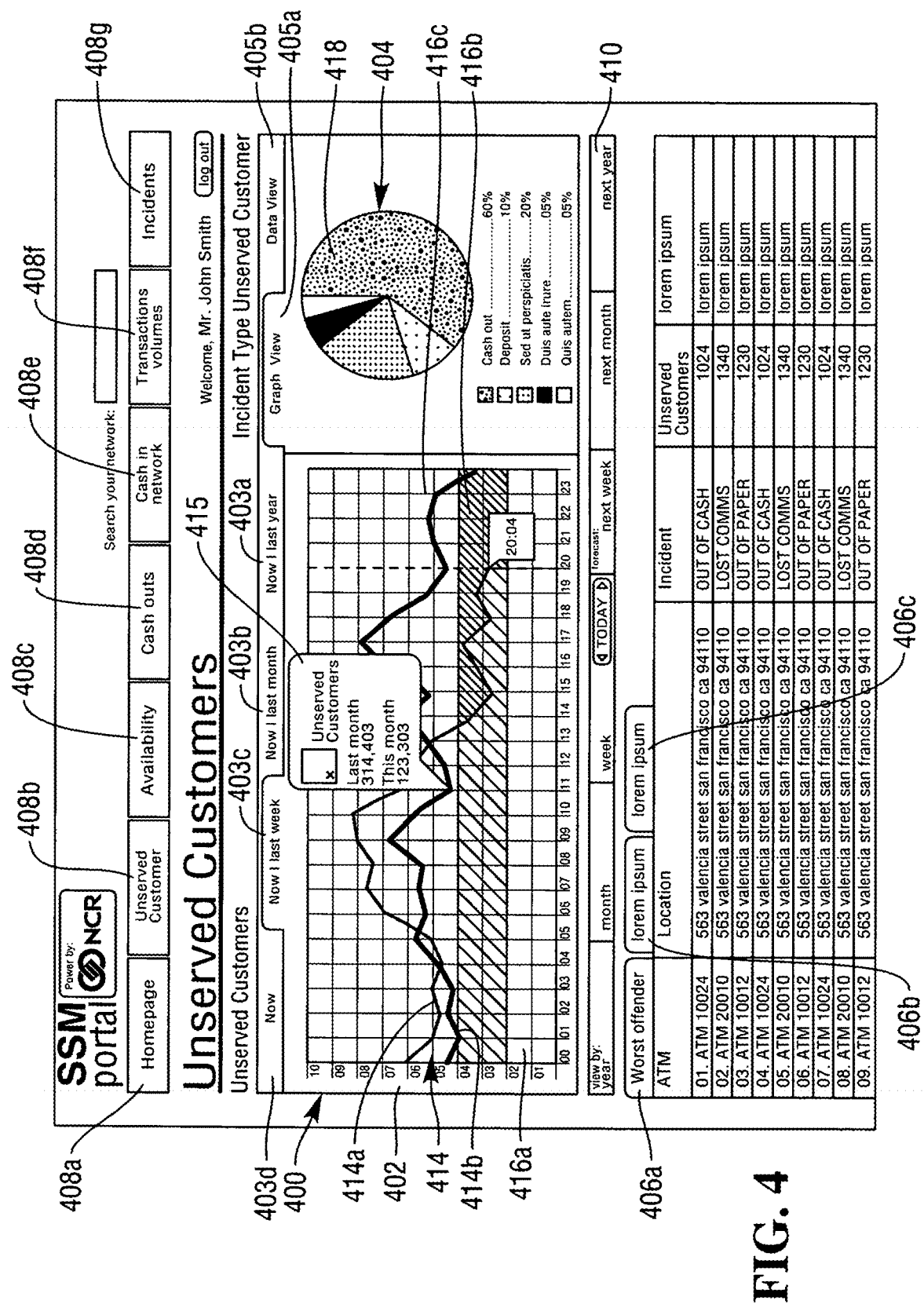
FIG. 4 is a screen shot of a second screen of the GUI portal of FIG. 3.
Figure 5:
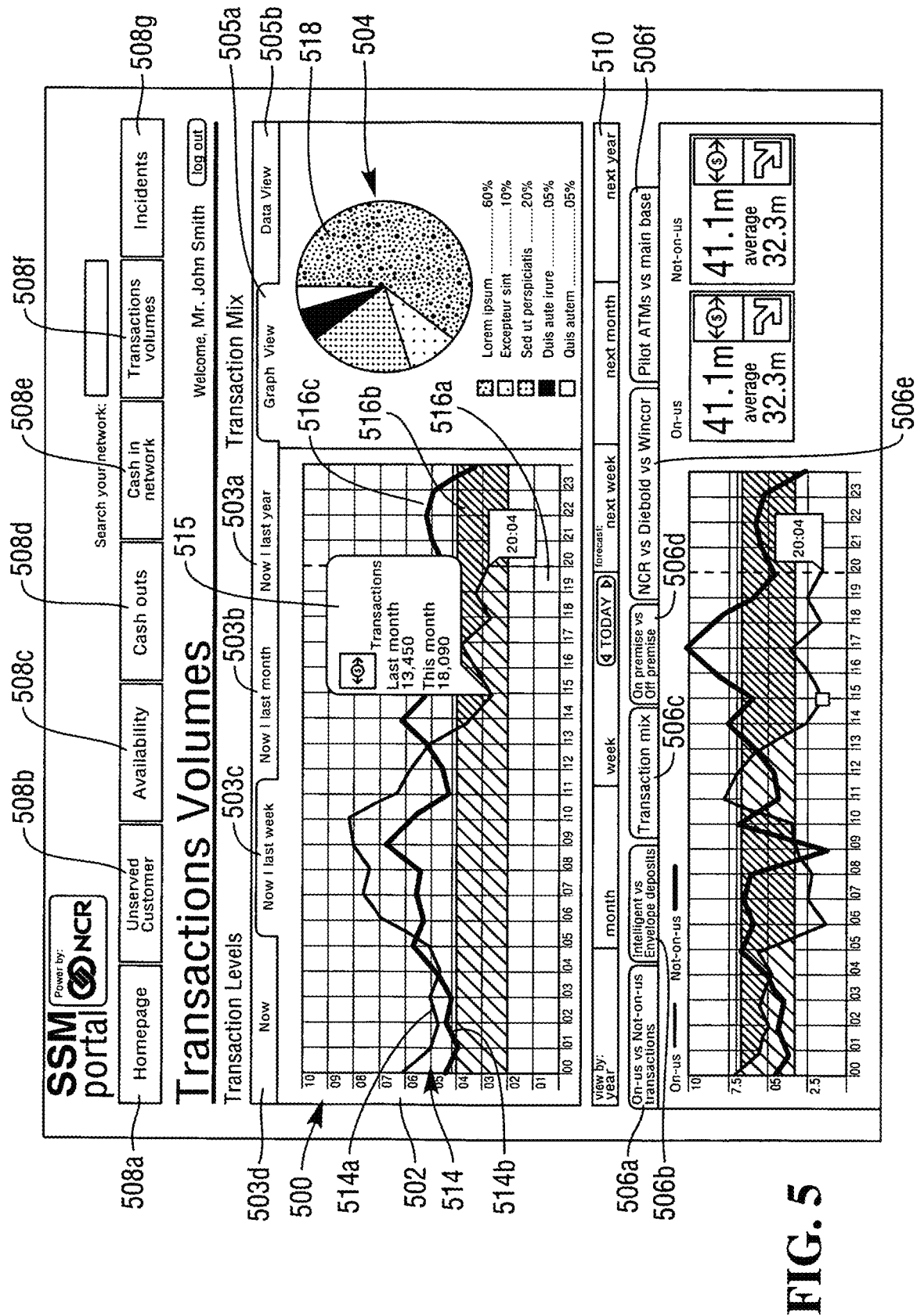
FIG. 5 is a screen shot of a third screen of a GUI portal of FIG. 3.

Referring now to FIGS. 3 to 5, a management portal GUI 300 displays a homepage 302. Typically, the homepage 302 is a webpage defined using standard languages such as html or XML. The homepage 302 comprises and active network map 304, a KPI dashboard 305, usage indicators 306, KPI tabs 308*a-g*, and priorities tabs 310*a-c*.

The active network map 304 comprises a graphical representation of a territory 312. A region 314 of the map 304 corresponding to, for example, a state, county, city or town, can be highlighted within the map 304. Typically, the region 314 is highlighted by hovering a cursor over the map 304 and clicking a button, either on a mouse or on the keyboard. Each region 314 has nodes 317 associated with either a single ATM or geographical grouping of ATMs. Such a geographical grouping may be based around a county, city, borough, or a town. Alternatively, nodes 317 may be based about a group of ATMs serviced by a particular maintenance operative.

A dialogue box 316 opens over the region 314. The dialogue box 316 contains a legend 318 that identifies the region 314 and icons 320 detailing KPIs of interest.

In some embodiments, it is envisaged that a user of the portal GUI 300 can drill down to a detailed map of the region 314 by use of a magnification bar 322. In an alternative embodiment, it is envisaged that drill down to detailed maps can be effected by, for example, multiple mouse clicks.

The usage indicators 306 give a graphical representation of total ATM usage metrics within the region 314.

The KPI dashboard 305 comprises graphical representations of KPIs, for example in the form of bar charts 324. The bar charts 324 comprise a first bar detailing the actual KPI metric 324*a*, and a second bar 324*b* detailing an acceptable threshold level. In at least one embodiment, the first bar 324*a* changes color, for example from green to red, when a threshold limit is crossed. The first bar 324*a* may also change color when a threshold limit is approached, typically from green to amber. It will be appreciated that the second bar 324*b* may be omitted if preferred.

The KPI dashboard 305 is updated periodically in response to performance data supplied by the management unit 106. The performance data supplied by the management unit 106 may be unadulterated performance data as received from the managed ATMs 102*a-d*, or it may be weighted performance data.

The KPI dashboard 305 can be updated at a frequency defined by the user of the portal 300, for example every thirty seconds, every five minutes etc.

As a user drills down geographically within the map 304 the KPI values detailed within the KPI dashboard 305 will change to reflect the region 314 being viewed within the map 304.

The KPI tabs 310*a-g* allow a user to switch between pages of the portal 300 detailing differing KPIs, in a manner known to those skilled in the art of web browsers.

The priorities tabs 312*a-c* allow a user to tab between windows within the homepage 302, in a manner known to those skilled in the are of web browsers. Typically, tabbing between windows is achieved by hovering a cursor over a tab 312*a-c* and clicking a mouse button.

When tabbed, a first of the tabs 312*a* causes a list 326 of the current top priority faults to be listed, fault priority having been determined as described hereinbefore. Typically, the list 326 shows the ATM type 328, the location of each ATM 330, the incident that has caused the outage 332, the number of unserved customers associated with the outage 334 and a further user definable field 336.

When tabbed, a second of the tabs 312*b* causes a template to be invoked, into which a user can enter priorities settings. Non-limiting, examples of priority settings include threshold limits, whether performance data uploaded from the management device 106 is to be unadulterated or weighted, and which KPIs are to be considered in determining priorities.

When tabbed, a third of the tabs 312*c* invokes a list of KPIs. Referring now to FIG. 4, an UC trend page 400 of the portal GUI 300 comprises a graphical trend window 402, comparison period tabs 403*a-d*, an UC breakdown window 404, view tabs 405*a,b*, user definable tabs 406*a-c*, KPI tabs 408*a-g*, and view period tabs 410.

The graphical trend window 402 displays a line graph 414 showing comparative figures of UC data 414*a*, 414*b* for a specified comparison period. The comparison period is defined by tabbing an appropriate comparison period tab 403*a-d*. Typical comparison periods are weekly, monthly, quarterly or yearly. A dialogue box 415 opens when a cursor is hovered over the line graph 414. The dialogue box 415 displays the comparative number of UCs at the point in the two comparison periods corresponding to the cursors position projected on to the abscissa. The line graph 414 has three bands 416*a-c*, the lowest band 416*a* is corresponds to an acceptable level of UC transactions, the middle band 416*b* corresponds to a level of UC transactions that causes concern and the upper level 416*c* represents an unacceptable level of UC transactions.

In the present example, UC data shown being compared between a current twenty four hour period, divided into hour long slots and the same period one week ago.

The UC breakdown window 404 displays either a graphical representation 418, or a textual breakdown of the transaction types that the UC transactions are expected to comprise based upon temporal usage data. The view tabs 405*a,b* are used to switch between the graphical or textual breakdowns. In the present embodiment the graphical breakdown of transaction types is in the form of a pie chart although it will be appreciated that any suitable form of graphical representation may be used, for example bar chart or line graph.

The user definable tabs 406*a-c* can be used to display whatever information is required by the user. In the present example the worst offending ATM in terms of UC transactions are displayed along with their location, the incident that caused the downtime and the calculated number of lost, or unserved, customers that the ATM downtime corresponds to.

The KPI tabs 408*a-g* allow a user to switch between pages of the portal 300 detailing differing KPIs, in a manner known to those skilled in the art of web browsers.

The view period tabs 410 allow a user to tab between viewing UC data for the prior time periods and also predicted UC data for the future. Such predicted UC data may be generated by modeling, the projection of historic date or a combination of the two.

Referring now to FIG. 5, a transaction volume trend page 500 of the portal GUI 300 comprises a graphical trend window 502, comparison period tabs 503*a-d*, a transaction volume breakdown window 504, view tabs 505*a,b*, user definable tabs 506*a-f*, KPI tabs 508*a-g*, and view period tabs 510.

The graphical trend window 502 displays a line graph 514 showing comparative figures of transaction volume data 514*a*, 514*b* for a specified comparison period. The comparison period is defined by tabbing an appropriate comparison period tab 503*a-d*. Typical comparison periods are weekly, monthly, quarterly or yearly. A dialogue box 515 opens when a cursor is hovered over the line graph 514. The dialogue box 515 displays the comparative transaction volume at the point in the two comparison periods corresponding to the cursors position projected on to the abscissa.

The line graph 514 has three bands 516*a-c*, the lowest band 516*a* is corresponds to unacceptably low transaction volumes, the middle band 516*b* corresponds to a transaction volume that causes concern and the upper level 516*c* represents an acceptable transaction volume In the present example, transaction volume shown are being compared over the current twenty four hour period, divided into hour long slots and the same period one week ago.

The breakdown window 504 displays either a graphical representation 518, or a textual breakdown of the transaction mix that the transaction volumes comprise. The view tabs 505*a,b* are used to switch between the graphical or textual breakdowns. In the present embodiment the graphical breakdown of transaction volumes is in the form of a pie chart, although it will be appreciated that any suitable form of graphical representation may be used, for example bar chart or line graph.

The user definable tabs 506*a-f* can be used to display whatever information is required by the user. In the present example they comprise "on-us vs not-on-us" transaction volumes 506*a*, deposit type 506*b*, transaction mix 506*c*, "on premise vs off premise" transaction volumes 506*d*, ATM supplier comparison 506*e* and location 506*f*.

Thus, these user definable tabs 506*a-f* allow a financial institution to compare statistics relevant to their concerns based upon any one of the KPIs graphically. For example, tabbing of the ATM supplier comparison tab 506*e* allows the financial institution to readily determine which of their ATM suppliers machines is more reliable, in terms of lost revenue, UC volumes or downtime dependent upon which statistic is configured to be displayed.

The KPI tabs 508*a-g* allow a user to switch between pages of the portal 300 detailing differing KPIs, in a manner known to those skilled in the art of web browsers.

The view period tabs 510*a-f* allow a user to tab between viewing transaction volume data for the prior time periods and also predicted transaction volume data for the future. Such predicted transaction volume data may be generated by modeling, the projection of historic date or a combination of the two.

The transaction volume page 500 is shown as an exemplar of a KPI page of the GUI portal 300. Differing KPI pages will have graphical displays commensurate with the information to be displayed in relation to the KPI selected.

It will be appreciated that each KPI page may have unique user defined statistical functions linked to their user definable tabs. However, there may be user defined statistical functions that are common across two or more KPI pages.

It is envisaged that each page, or pane within a page, can be selectively highlighted to be saved independently, for example as a PDF file or a JPEG file.

It will be further appreciated that although described with reference to an SNMP architecture the present invention may be implemented using any suitable communication architecture, for example web services or a proprietary messaging interface.

It will be appreciated that although described with reference to a distributed network of ATMs the present invention can be any suitable managed network of self-service terminals, for example medical record entry terminals or self-check in/out terminals.

Various modifications may be made to the above described embodiment within the scope of the invention without departing from the spirit of the invention.

The invention claimed is:

1. A device management system comprising:
 a processor;
 a data storage device; and
 a network connection;
 wherein, the data storage device being arranged to store
  weighting data associated with at least one managed device, the processor being arranged to receive performance metric data from the at least one managed device via the network connection, the performance metric data including: transaction volumes for the at least one managed device, transaction approval rates for the at least one managed device, session time per transaction on the at least one managed device, and incidents causing outages for the at least one managed device, the processor being arranged to access the weighting data from the data storage device and being further arranged to weight a portion of the performance metric data associated with the at least one managed device with respect to a portion of weighting data associated with the at least one managed device, to produce weighted performance data, the processor also is arranged to process the weighted performance data to prioritize events occurring on the at least one managed device, and wherein the processor is configured and arranged to schedule maintenance for the at least one managed device based on the prioritized events;

wherein the processor is configured to output a graphical user interface (GUI) to a display device and to present: a physical location of the at least one managed device, a status indicator for the at least one managed device with values representing each of the performance metric data, a weighted value for the weighted performance data, and temporal trend data for the weighted performance data over time.

2. The system of claim 1, wherein at least one managed device comprises a self-service device.

3. The system of claim 2, wherein the self-service device comprises at least one of the following: an ATM, a medical record entry terminal or a self-check in/out terminal.

4. The system of claim 1 wherein the weighting data comprises at least one of the following:
   temporal usage data corresponding to a period over which the performance metric data was acquired, fee data corresponding to a fee associated with a transaction, temporal accessibility data corresponding to time periods when the at least one managed device is operable by a user, location data indicative of geographic factors associated with the at least one managed device.

5. The system of claim 1, wherein the weighted performance data comprises a measure of the number of users unable to perform a transaction at the managed device during a period of downtime of the at least one managed device.

6. The system of claim 1, wherein the weighted performance data comprises a measure of revenue lost by an operator of the at least one managed device during a period of downtime of the at least one managed device.

7. The system of claim 4, wherein the temporal usage data comprises historical usage data.

8. The system of claim 4, wherein the temporal usage data comprises projected usage data.

9. The system of claim 1, wherein the processor is further arranged to rank a plurality of managed devices with respect to values of at least one common weighted performance data set.

10. A device management method implemented in a non-transitory computer-readable medium as executable instructions processed by a computing device, the computing device performing the method:
   weighting, by the computing device, performance metric data, associated with at least one managed device with respect to a respective portion of weighting data associated with the at least one managed device;
   producing weighted performance data;
   prioritizing events at the at least one managed device using the weighted performance data;
   scheduling maintenance for the at least one managed device and other managed devices based on the prioritized events; and
   outputting a graphical user interface (GUI) to a display device that presents and graphs the weighted performance data, provides and presents a physical location for the at least one managed device, and provides and presents status indicators having a value for each of the performance metric data.

11. The method of claim 10, wherein weighting further includes weighting the performance metric data by using one or more of: temporal usage data corresponding to a period over which the performance metric data was acquired, fee data corresponding to a fee associated with a transaction, temporal accessibility data corresponding to time periods when the at least one managed device is operable by a user, location data indicative of geographic factors associated with the at least one managed device.

12. The method of claim 10 further comprising, calculating, by the computing device, an estimate of number of users unable to perform a transaction at the managed device during a period of downtime of the at least one managed device, using the weighted performance data.

13. The method of claim 10 further comprising, calculating, by the computing device, an estimate of revenue lost by an operator of the at least one managed device during a period of downtime of the at least one managed device, using the weighted performance data.

14. The method of claim 10 further comprising, ranking, by the computing device, a plurality of managed devices with respect to values of at least one common weighted performance data set.

15. The method of claim 10, wherein weighting further includes identifying the at least one managed device as a self-service device.

16. The method of claim 15, wherein identifying further includes recognizing the self-service device as one of: an Automated Teller Machine (ATM), a medical record entry terminal or a self-check in/out terminal.

* * * * *